(12) United States Patent
Wabel et al.

(10) Patent No.: US 10,376,176 B2
(45) Date of Patent: Aug. 13, 2019

(54) DEVICE HAVING ELECTRODES FOR BIO-IMPEDANCE MEASUREMENT FOR DIALYSIS

(71) Applicant: FRESENIUS MEDICAL CARE DEUTSCHLAND GMBH, Bad Homburg (DE)

(72) Inventors: Peter Wabel, Darmstadt (DE); Paul Chamney, Herts (GB); Tobias Groeber, Heusenstamm (DE); Ulrich Moissl, Karben (DE); Sebastian Wieskotten, Ober-Ramstadt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 14/397,439

(22) PCT Filed: Apr. 26, 2013

(86) PCT No.: PCT/EP2013/001257
§ 371 (c)(1),
(2) Date: Oct. 27, 2014

(87) PCT Pub. No.: WO2013/159935
PCT Pub. Date: Oct. 31, 2013

(65) Prior Publication Data
US 2015/0164370 A1 Jun. 18, 2015

Related U.S. Application Data
(60) Provisional application No. 61/638,514, filed on Apr. 26, 2012.

(30) Foreign Application Priority Data
Apr. 26, 2012 (EP) ..................... 12002955

(51) Int. Cl.
*A61B 5/053* (2006.01)
*A61M 1/28* (2006.01)
(Continued)

(52) U.S. Cl.
CPC .......... *A61B 5/0537* (2013.01); *A61B 5/4875* (2013.01); *A61M 1/14* (2013.01);
(Continued)

(58) Field of Classification Search
CPC ... A61B 5/0537; A61B 5/4875; A61B 5/4836; A61M 1/14–32; A61M 1/28; A61M 1/282; A61M 1/284
(Continued)

(56) References Cited

U.S. PATENT DOCUMENTS 4,008,712 A * 2/1977 Nyboer ................ A61B 5/0537 600/547
4,370,983 A * 2/1983 Lichtenstein ............ A61B 5/00 600/301
(Continued)

FOREIGN PATENT DOCUMENTS

| CN | 1593336 | 3/2005 |
| CN | 1849092 | 10/2006 |

(Continued)

OTHER PUBLICATIONS

International Search Report in PCT/EP2013/001257, dated Aug. 6, 2013.
(Continued)

*Primary Examiner* — Devin B Henson
(74) *Attorney, Agent, or Firm* — Fish & Richardson P.C.

(57) ABSTRACT

Electrodes for a bio-impedance measuring device or a body composition monitor, the electrodes being integral with or being attached to a surface of at least one device belonging to a group of electronic and/or non-electronic devices used
(Continued)

in the preparation of a dialysis treatment or during dialysis, in particular during peritoneal dialysis, the group preferably consisting of organizers of a continuous ambulatory peritoneal dialysis system (CAPD), automated peritoneal dialysis devices, automated peritoneal dialysis-cyclers (APD-Cycler), bioelectrical impedance analyzers (BIA), body composition monitors (BCM), hand-held electrodes holders for the electrodes, and dialysis apparatuses. Devices and methods used during dialysis are also described.

15 Claims, 4 Drawing Sheets

(51) Int. Cl.
   *A61B 5/00* (2006.01)
   *A61M 1/14* (2006.01)
(52) U.S. Cl.
   CPC .............. *A61M 1/28* (2013.01); *A61M 1/282* (2014.02); *A61M 1/284* (2014.02); *A61B 5/4836* (2013.01); *A61B 2560/0468* (2013.01); *A61M 2205/3303* (2013.01); *F04C 2270/041* (2013.01)
(58) Field of Classification Search
   USPC ......................................................... 600/547
   See application file for complete search history.

(56) References Cited

U.S. PATENT DOCUMENTS

| | | | | |
|---|---|---|---|---|
| 5,580,460 | A * | 12/1996 | Polaschegg | A61M 1/16 210/138 |
| 5,613,463 | A * | 3/1997 | Stokes | G09F 11/23 116/201 |
| 5,788,643 | A * | 8/1998 | Feldman | A61B 5/4869 128/898 |
| 6,243,651 | B1 * | 6/2001 | Masuo | A61B 5/0537 600/547 |
| 6,615,077 | B1 * | 9/2003 | Zhu | A61B 5/022 600/547 |
| 6,790,178 | B1 * | 9/2004 | Mault | A61B 5/0011 128/903 |
| 6,963,035 | B2 * | 11/2005 | Honda | A61B 5/0537 128/920 |
| 7,354,417 | B1 | 4/2008 | Levin et al. | |
| 9,020,827 | B2 * | 4/2015 | Elahi | A61M 1/28 705/2 |
| 2003/0120170 | A1 * | 6/2003 | Zhu | A61B 5/0537 600/547 |
| 2005/0070778 | A1 | 3/2005 | Lackey et al. | |
| 2005/0085742 | A1 * | 4/2005 | Ueda | A61B 5/0537 600/547 |
| 2005/0090760 | A1 * | 4/2005 | Kobayashi | A61B 5/053 600/547 |
| 2007/0027402 | A1 * | 2/2007 | Levin | A61B 5/0537 600/547 |
| 2009/0118594 | A1 | 5/2009 | Zdeblick | |
| 2009/0182204 | A1 | 7/2009 | Semler et al. | |
| 2010/0198100 | A1 * | 8/2010 | Oku | A61B 5/0537 600/547 |
| 2010/0234701 | A1 * | 9/2010 | Cho | A61B 5/01 600/301 |
| 2010/0256516 | A1 * | 10/2010 | Kasahara | A61B 5/0537 600/547 |
| 2010/0298662 | A1 * | 11/2010 | Yu | A61M 1/28 600/301 |
| 2011/0208097 | A1 | 8/2011 | Farese et al. | |
| 2011/0213268 | A1 * | 9/2011 | Kosaka | A61B 5/0537 600/547 |
| 2012/0035432 | A1 * | 2/2012 | Katra | A61B 5/0538 600/301 |
| 2012/0157867 | A1 * | 6/2012 | Pekonen | A61B 5/0428 600/509 |
| 2013/0204098 | A1 * | 8/2013 | Chamney | A61B 5/0537 600/301 |
| 2013/0204298 | A1 | 8/2013 | Graul et al. | |
| 2013/0215042 | A1 * | 8/2013 | Messerschmidt | G06F 3/041 345/173 |
| 2013/0217993 | A1 * | 8/2013 | Brunner | A61B 5/0536 600/393 |

FOREIGN PATENT DOCUMENTS

| | | | | |
|---|---|---|---|---|
| DE | 10-2009-026224 | | 2/2011 | |
| DE | 1020100031530 A1 | | 1/2012 | |
| WO | 2009/036321 A1 | | 3/2009 | |
| WO | WO 2011/113169 A1 * | | 9/2011 | A61B 5/053 |

OTHER PUBLICATIONS

International Search Report in International Application No. PCT/EP2013/001257, dated Aug. 6, 2013, 4 pages (with English translation).

Crepaldi et al., "Application of Body Composition Monitoring to Peritoneal Dialysis Patients", Peritoneal Dialysis—From Basic Concepts to Clinical Excellence 163: Jan. 1-6, 2009.

\* cited by examiner

DEVICE HAVING ELECTRODES FOR BIO-IMPEDANCE MEASUREMENT FOR DIALYSIS

CROSS REFERENCE TO RELATED APPLICATIONS

The present application is the national stage entry of International Patent Application No. PCT/EP2013/001257, filed on Apr. 26, 2013, which claims priority to European Application No. EP 120 02 955, filed on Apr. 26, 2012, and claims priority to U.S. Provisional Patent Application Ser. No. 61/638,514, filed on Apr. 26, 2012, the disclosures of which are expressly incorporated herein in its entirety by reference thereto.

FIELD OF INVENTION

The present invention relates to electrodes for realizing at least one bioelectrical impedance analysis to estimate the hydration and/or the nutritional status of dialysis patients before, during or after dialysis treatment. It further relates to a device to be used before or during dialysis or while preparing a dialysis treatment, in particular peritoneal dialysis, ultrafiltration, hemofiltration, hemodiafiltration, hemo-ultrafiltration or hemodialysis, to a dialysis apparatus and to a method for determining parameters for estimating the hydration or the nutritional status of a dialysis patient. The present invention further relates to a non-transitory computer-readable medium with an executable program stored thereon, to a computer program and to a computer program product comprising computer program code.

BACKGROUND INFORMATION

In certain treatment procedures such as dialysis (hereinafter, this term and the term dialysis treatment each encompass peritoneal dialysis, ultrafiltration, hemodialysis, hemofiltration, Hemo-ultrafiltration, hemodiafiltration and the like) excess body fluid is removed from the patient's body. An accurate knowledge of the patient's hydration state before starting a treatment session is desirable for determining the most appropriate dialysis treatment, for controlling of the dialysis apparatus, and for determining and achieving the patient's post treatment target weight.

For example, peritoneal dialysis is often conducted by the patient alone at home and without being constantly monitored or supervised by medically trained staff. In fact, home peritoneal dialysis patients are seen by the dialysis staff in charge only every 4-12 weeks. Therefore, hydration state measurements made in a professional setting are made only every now and then. For that reason, it is particularly important for peritoneal dialysis to be provided with accurate methods and devices in order to easily determine by oneself the present hydration state between examinations that are carried out by the medical staff every 4-12 weeks.

There are some methods available to estimate the hydration state of a patient including assessment of weight changes, edema, jugular venous pressure, blood pressure, the measurement of hematocrit, of natriuretic peptides (ANP, Pro-BNP, and BNP), cyclic guanidine monophosphate (cGMP) and/or inferior vena cava diameter. These methods are not all clinically useful because of limited accuracy or practicability or both.

The estimation of the patient's hydration (also referred to as the patient's hydration state) before a dialysis treatment session using bio-impedance analysis can be a useful step toward revealing the patient's hydration status. Bio-impedance techniques measuring body fluid content are advantageous in that they are non-invasive, relatively cheap, generally easily to perform and reliable if carried out correctly. Further they can in theory be carried out by the patient himself and even without professional supervision. However, these clinical methods are still too cumbersome for some patients. Also, when carried out, the results depend strongly on how accurately the electrodes used for the bio-impedance measurement are placed by the patient. In practice, it has turned out that a number of patients are not capable of using the electrodes which have to be placed on both arms, one arm and one foot, both feet, or the like in the intended manner. In consequence, the results stemming from bio-impedance measurements—if carried out at all—and their interpretation can suffer remarkably.

SUMMARY

It is therefore an object of the present invention to provide electrodes intended for a bioelectrical impedance measurement and to suggest devices for a bioelectrical impedance measurement or for a dialysis treatment or both, and a corresponding method.

The electrodes according to the present invention, i.e., one, two, or more electrodes, or one, two, or more pairs of electrodes, for a bio-impedance measuring device are being intended and/or prepared to be used with a bio-impedance measuring device. The electrodes are integral with or attached to or into a portion or a surface (or intended to be attached) of at least one device selected from a group of electronic and/or non-electronic devices used in the preparation of a dialysis treatment or during dialysis of any kind as set forth above, for example during peritoneal dialysis or hemodialysis. In some embodiments according to the present invention, said group consists of at least one item of organizers of a continuous ambulatory peritoneal dialysis system (CAPD), organizer for so-called stay-safe-dialysis-bags, automated peritoneal dialysis devices, automated peritoneal dialysis-cyclers (APD-Cycler), bioelectrical impedance analyzers (BIA), body composition monitors (BCM), hand-held electrodes holders for the electrodes and dialysis apparatuses.

A 'dialysis apparatus' or a 'dialysis machine' or 'dialysis device' within the meaning of the present invention may be an apparatus configured or embodied for carrying out a dialysis treatment within the meaning thereof as set forth above. Hence, a dialysis apparatus or machine according to the present invention may be a peritoneal dialysis machine, a hemodialysis machine, a hemofiltration machine, a hemo-ultrafiltration machine, a hemodiafiltration machine and the like or combinations thereof.

The device according to the present invention is used during dialysis or while preparing a dialysis treatment or intended to be used during dialysis or while preparing a dialysis treatment, in particular peritoneal dialysis or any other kind of dialysis. The device comprises at least one (or two or more) integrated and/or attached electrode or pairs of electrodes according to the present invention.

The dialysis apparatus according to the present invention comprises at least one electrode according to the present invention, the device according to the present invention, or both, or is in signal communication therewith to receive results of measurements carried out by means of the electrodes.

The method for determining parameters for estimating the hydration or the nutritional status of a dialysis patient according to the present invention encompasses touching at least two electrodes according to the present invention with at least two body portions while the electrodes are connected to a bioelectrical impedance analyzer or a body composition monitor or both. The method further comprises collecting and processing the information gained by of the electrodes in a processing element in at least one bioelectrical impedance analyzer and/or body composition monitor.

The present invention also relates to a non-transitory computer-readable medium with an executable program stored thereon, wherein the program instructs a programmable computer system to perform the steps of any of the embodiments of the method according to the present invention as described herein.

The present invention also relates to a computer program and to a computer program product comprising computer program code portions adapted to perform any of the embodiments of the method according to the present invention as described herein.

The present invention also relates to the use of the electrodes according to the present invention, of the device according to the present invention and of the dialysis apparatus according to the present invention.

The use of the expression 'may be' or 'may have' and so on, is to be understood herein synonymously with 'preferably is' or 'preferably has', respectively, and so on, and is intended to illustrate exemplary embodiments according to the present invention.

Embodiments according to the present invention may comprise one, some or all of the following features in arbitrary combinations.

In some embodiments according to the present invention, if reference is made to "the steps of any of the embodiments of the method according to the present inventions", in particular in connection with the non-transitory computer-readable medium with an executable program stored thereon, the computer program or the computer program product comprising computer program code, "the steps" may be understood as referring only to steps that will be carried out by a device or in an automatic manner.

In certain embodiments according to the present invention, the non-transitory computer-readable medium with an executable program stored thereon comprises electrodes, a processor and/or any other device needed for carrying out the steps, or is connected therewith.

In some embodiments, the electrodes according to the present invention are detachably attached to the electronic and/or a non-electronic device.

In certain embodiments, the electrodes according to the present invention are non-detachably attached to the electronic and/or a non-electronic device.

In some embodiments according to the present invention, at least one electrode is a non-disposable and/or reusable electrode or intended to be used several times without being removed from a surface it has been attached to in the time between two measurements (taking place on different days).

In certain embodiments according to the present invention, a first electrode and a second electrode are integrated or arranged having a distance between them which is particularly in the range of 2.5 to 15 cm, and more particularly in a range of 4 to 7.5 cm.

In some embodiments, the electrodes according to the present invention have at least one connection element intended and/or configured to connect at least one electrode to at least one bioelectrical impedance analyzer or to at least one body composition monitor or both.

In certain embodiments according to the present invention, a first electrode and a second electrode are arranged on different surfaces of the electronic or non-electronic device.

In some embodiments according to the present invention, these surfaces are the front side and rear side, in others these surfaces are the left and the right side, the upper and the bottom side or any combination of two arbitrary sides mentioned herein.

In certain embodiments, the device according to the present invention is selected from a group consisting of organizers of a continuous ambulatory peritoneal dialysis system, automated peritoneal dialysis devices, automated peritoneal dialysis-cyclers, dialysis machines, and hand-held electrodes holders.

In some embodiments according to the present invention, the device is or comprises a bioelectrical impedance analyzer or body composition monitor or both or is—in a wireless or a non-wireless manner—connected thereto.

In certain embodiments according to the present invention, the device is configured or arranged, e.g., by means of a corresponding device, to start measuring the bioelectrical impedance and/or the body composition measurements automatically upon touching one, at least one, two, three, four or more of the electrodes by the patient. To this end, in particular embodiments according the present invention sensors are provided which detect the presence of the fingers or other body sections of the patient on the device. The presence may be detected by resistance, skin resistance, skin temperature, pressure or the like. The presence may also be detected by contact buttons which close an electrical circuit once they are touched or pressed by the patient.

In some embodiments according to the present invention, the device comprises a button or switch or element that has to be pushed, switched, inserted, attached or otherwise activated or operated before a bioelectrical impedance and/or body composition measurement may be started at all. The activation or operation of the button, switch or element may be a pre-condition necessary to bring the device into a mode in which the measurement can be started (whereas the measurement cannot be started before this mode has been selected). Of course, it may be provided that for starting the measurement it may not be sufficient that the system has entered into above mentioned modus; additionally some action from the patient may be required such as touching some sensors as described above, or the like.

In certain embodiments according to the present invention, for starting the bioelectrical impedance and/or body composition measurement a disc with a dial or another element such as a connector, for example a so-called stay safe connector (which may be a part or a disc of a so-called stay safe (organizer) which is commercially distributed by Fresenius Medical Care, Germany), has to be inserted into or connected with the device according to the present invention. The connector, disc or element may have the function of a key such that a measurement cannot be started before the 'key' is connected with the device. The connector, disc or element may be required to start a treatment in which the device according to the present invention is used.

In some embodiments according to the present invention, it may be provided that it is not sufficient to have the connector, the disc or another element inserted into or connected with the device. In these embodiments according to the present invention, it might be requested that the connector, the disc or the element has to be brought into a particular position on the device before measuring the bioelectrical impedance and/or body composition is enabled. For example, the disc might have to be rotated into a pre-set position or the element, if embodied as a switch, might have to be switched in a predetermined manner. In certain embodiments according to the present invention, a device for checking whether the connector, the disc or the element is in the pre-set position or not is provided. For example, the disc may have to be connected with the device and be turned into a pre-determined position before the patient is allowed to measure his bioelectrical impedance and/or body composition.

In certain embodiments according to the present invention, an element of the device such as a switch for selecting between two or more operating states or modes of the device may be provided. Based on the operating state that is presently selected by means of the switch a measurement may be allowed or blocked. In some embodiments according to the present invention, a sensor is provided for detecting in which operating state or modus the device is.

Since the results achieved by a bioelectrical impedance and/or body composition measurement may depend on circumstances such as a stage of a simultaneously conducted dialysis treatment, and since measurements conducted during some stages of the treatment might result in different findings compared to the measurements conducted during other stages of the same treatment session, in some embodiments of the present invention the patient is given an acoustical, optical or any other hint indicating that a bioelectrical impedance and/or body composition should or should not be carried out right now, or the like. For example, the patient might be informed by a tone or any other signal that he should start his measurement now. Such a signal might be given, e. g., right before his peritoneum is going to be filled or emptied or while the peritoneum is emptied. The signal might be sent based on the operating state of the device or the treatment device as detected by a suitable sensor.

In some embodiments according to the present invention, the device comprises another device for sending a measurement result to a dialysis machine, to a medical monitoring centre, the doctor in charge, to a clinic, to a hospital, to a dialysis centre, and/or the like.

In certain embodiments according to the present invention, the measurement results are sent or signaled in a wireless manner.

In some embodiments according to the present invention, the device comprises another device for sending a warning signal (a text message, for example, or any other signal) to a medical monitoring centre, the doctor in charge, to a clinic, to a hospital, to a dialysis centre, and/or the like, once the measurement results have exceeded an upper or lower threshold. This allows an easy determination for the remote working recipient to assess if or when the patient should be seen by a doctor or by medical staff in general.

In particular embodiments according to the present invention, the dialysis apparatus is an apparatus for peritoneal dialysis, hemodialysis, hemofiltration, and/or hemodiafiltration or for any other dialysis treatment as set forth above.

In certain embodiments according to the present invention, the dialysis apparatus comprises a control unit, the control unit being configured to control—with or without feedback control—the dialysis treatment based on the signal representing the results of the measurement carried out by means of the electrodes.

In some embodiments of the method according to the present invention, the at least two body portions for touching the at least two electrodes according to the present invention are two fingers of one hand, or at least two fingers of different hands, or two fingers of each hand, or any part of a hand and any part of a foot, or any part of both feet, or another two separate parts of the body.

In certain embodiments, the method according to the present invention encompasses manually inputting information into the bioelectrical impedance analyzer and/or to the body composition monitor about the patient's parameters as for example height, weight, age, sex and/or with what part of the patient's body the electrodes have been touched.

In some embodiments, the method according to the present invention additionally comprises adjusting the treatment parameters of a dialysis treatment to the results of the bioelectrical impedance analysis.

In certain embodiments, the method according to the present invention comprises starting the bioelectrical impedance measurement solely by touching at least one electrode, two electrodes or two pairs of electrodes.

In some embodiments, the method according to the present invention comprises adjusting or controlling the dialysis treatment in an automatic manner based on a measurement result achieved by the method according to the present invention.

In certain embodiments, the method according to the present invention comprises filtering of the measurement results and in particular of the measured body resistance or any other mathematical scatter or noise reduction. This may enhance the accuracy of the input data used for a subsequent determination of the overhydration (herein also referred to as the overhydration state) or used for a body composition calculation, and for giving the patient a more precise feedback on his status.

The filtering or mathematical scatter or noise reduction may encompass the use of a Kalman filter, a mean, an average, or the like and combination thereof.

In certain embodiments, the method according to the present invention comprises obtaining first bioimpedance measurement data of a patient from a first type of bioimpedance measurement, deriving bioimpedance calibration data from the first bioimpedance measurement data for calibrating second bioimpedance measurement data from a second type of bioimpedance measurement, obtaining the second bioimpedance measurement data from a second bioimpedance measurement of the patient, and calibrating the second bioimpedance measurement data using the calibration data to determine the overhydration parameter or the body composition parameter of the patient.

In some embodiments according to the present invention the step of obtaining first bioimpedance measurement data comprises performing a first bioimpedance measurement.

In certain embodiments, the method according to the present invention the step of performing a first bioimpedance measurement comprises measuring a bioimpedance spectrum of the patient at one frequency or at multiple frequencies.

In some embodiments, the method according to the present invention comprises receiving bioimpedance calibration data derived from first bioimpedance measurement data obtained by a first type of bioimpedance measurement, the bioimpedance calibration data being suitable for calibrating second bioimpedance measurement data from a second type of bioimpedance measurement, obtaining the second bioimpedance measurement data from a second bioimpedance measurement of the patient and calibrating the second bioimpedance measurement data using the calibration data to determine the overhydration parameter or the body composition parameter of the patient.

In certain embodiments, the method according to the present invention the step of obtaining the second bioimpedance measurement data comprises performing a second bioimpedance measurement.

In certain embodiments, the method according to the present invention the step of performing a second bioimpedance measurement comprises measuring a bioimpedance of the patient at a single frequency.

In certain embodiments, the method according to the present invention comprises obtaining a plurality of bioimpedance measurements of the second type at different times to generate a time series of bioimpedance measurements, performing time analysis of the time series to determine whether a current bioimpedance measurement of the time series deviates significantly from previous bioimpedance measurements of the time series, and generating an indication that a new measurement of the first type of bioimpedance measurements should be performed or a warning message.

In certain embodiments, the method according to the present invention the step of deriving the calibration data comprises using bioimpedance reference data correlating bioimpedance measurement results of the first type and bioimpedance measurement results of the second type.

In certain embodiments, the method according to the present invention comprises a step of deriving the reference data, wherein the first type of bioimpedance measurements comprises a first type of electrode configuration, wherein the second type of bioimpedance measurements comprises a second type of electrode configuration, and wherein the step of deriving the reference data comprises applying a conversion factor between a first format considering a measurement using the first type of electrode configuration and a second format considering a measurement using the second type of electrode configuration.

In some embodiments, the method according to the present invention comprises obtaining the first bioimpedance measurement data, deriving the bioimpedance calibration data from the first bioimpedance measurement data, providing the bioimpedance calibration data to a device for determining the overhydration parameter or the body composition parameter.

In some embodiments, the method according to the present invention comprises performing a plurality of bioimpedance reference measurements, each comprising a first reference measurement of the first type of bioimpedance measurement and a second reference measurement of the second type of bioimpedance reference measurement and correlating data from the first and the second reference measurements to obtain the bioimpedance reference data.

The devices, apparatuses and machines according to the present invention comprise in particular embodiments of the present invention devices, monitors and the like which are adapted and/or configured for carrying out at least one or all of the steps described in here.

For example, the device or the dialysis apparatus according to the present invention comprises in some embodiments a data provisioning unit for obtaining first bioimpedance measurement data of a patient from a first type of bioimpedance measurement, a processing unit for deriving bioimpedance calibration data from the first bioimpedance measurement data for calibrating second bioimpedance measurement data from a second type of bioimpedance measurement, a data obtaining unit for obtaining the second bioimpedance measurement data from a second bioimpedance measurement of the patient, and a calibration unit for calibrating the second bioimpedance measurement data using the calibration data to determine the overhydration parameter or the body composition parameter of the patient.

In certain embodiments of the present invention, the device or the dialysis apparatus according to the present invention or both comprise a measurement unit for performing a bioimpedance measurement for obtaining the first bioimpedance measurement data.

In certain embodiments of the present invention, the measurement unit is adapted to measure the bioimpedance spectrum of the patient at multiple frequencies.

The device or the dialysis apparatus according to the present invention comprises in some embodiments a receiving unit for receiving bioimpedance calibration data derived from first bioimpedance measurement data obtained by a first type of bioimpedance measurement, the bioimpedance calibration data being suitable for calibrating second bioimpedance measurement data from a second type of bioimpedance measurement, a data obtaining unit for obtaining the second bioimpedance measurement data from a second bioimpedance measurement, of the patient, and a calibration unit for calibrating the second bioimpedance measurement data using the calibration data to determine the overhydration parameter or the body composition parameter of the patient.

In certain embodiments of the present invention, the device or the dialysis apparatus according to the present invention comprises a measurement unit for performing a bioimpedance measurement for obtaining the second bioimpedance measurement data.

In some embodiments of the present invention, the measurement unit is adapted to measure the bioimpedance of the patient at a single frequency.

In certain embodiments according to the present invention the expressions 'bio-impedance analyzer', 'bioelectrical impedance analyzer', 'bio-impedance measuring device' and 'bio-impedance analysis', or 'bioelectrical impedance analysis' relate to bio-impedance measuring devices or bioelectrical impedance analysis methods that are known in the art. In some embodiments according to the present invention, such devices use the 50 kHz current frequency vector and/or the multifrequency bio-impedance measurement or spectroscopy.

In some embodiments according to the present invention, the bio-impedance measuring device is a monitor as described in WO 2006/002685 A1. The respective disclosure of WO 2006/002685 A1 is hereby incorporated in the present application by way of reference. Of course, the present invention must not be understood to be limited to monitors obtaining data by bio-impedance measurements as is described in WO 2006/002685 A1. Other bio-impedance measurement methods known in the art and also any other devices known in the art are also contemplated and encompassed by the present invention.

In certain embodiments according to the present invention, the bio-impedance measuring device is configured to measure the extracellular fluid volume over total body water (ECV/TBW) ratio, extracellular fluid volume over body mass (ECV/BM), and/or extracellular over intracellular volume (ECV/ICV).

In some embodiments according to the present invention, the device according to the present invention and/or the dialysis apparatus according to the present invention comprise a device for signaling or sending the measurement results achieved by means of the method according to the present invention to an electronic medical card of the patient comprising personal and/or treatment data of the patient for saving or storing the measurement results for a later use thereof.

The present invention also relates to devices, apparatuses, and the like, which are adapted, configured, arranged, programmed or the like to carry out each of the methods according to the present invention or single steps thereof.

Any embodiment according to the present invention may have one or more of the above or in the following mentioned advantages in any combination.

Since the electrodes intended for measuring the body's resistance at one or more frequencies or for measuring the bio-impedance of a patient's body by a bio-impedance measuring device are suggested herein to be integral with or permanently attached to at least one device of the above mentioned group according to the present invention, the patient does not need help in placing the electrodes on his limbs. Rather, it is quite easy to handle and use the electrodes and the devices according to the present invention. Therefore, the patient is capable of measuring his body fluid content whenever and as frequently as he wishes to. This is believed to increase the patient's compliance regarding using the device for measuring on a frequent basis. This may obviously result in higher quality treatment.

Also, since the patient does not have to place the electrodes anywhere on his limbs but has only to put his fingers or other parts of the body onto electrodes that are both attached to a device and determined to be used in a particular way, the patient cannot fail to use the electrodes in the only correct manner. This obviously results in higher quality measurements. Besides, the measurements carried out are performed in a reproducible way. The results achieved can be compared to results gained earlier in a more reliable manner.

Further, since the electrodes according to the present invention are intended to be used more often than only once—in contrast to disposable electrodes known from the prior art—and since they may be reusable, waste material does not have to be disposed of after every single measurement. This implies the advantages well-known to the skilled person.

The electrodes according to the present invention may have a shape that only allows their use by pre-defined parts of the body, e. g. the fingers. Hence, the accuracy of the measurements carried out by means of those electrodes may be enhanced as their shape does not allow for contact with other body parts, e.g., the foot if this was not intended by the manufacturer.

Also, if at least some electrodes according to the present invention are arranged on different surfaces of the electronic or non-electronic device of the above mentioned group, for example both on the front side and on the rear side, an incorrect use of the electrodes is further ruled out. Again this may lead to better measurement results.

In certain embodiments of the present invention, the devices comprise a device for signaling or sending the measurement results to a medical monitoring centre, to the doctor in charge, to a clinic, to a hospital, to a dialysis centre, and/or the like. Any of those recipients—such as the medical monitoring centre—can check for plausibility of the results, developments of the body fluid content and the like and contact and inform the patient if necessary to prevent harm.

If, as is also contemplated by embodiments of the present invention, the devices according to the present invention comprise a device for signaling or sending the measurement results to a dialysis apparatus, the device or the dialysis apparatus can check for plausibility of the results, develop-ments of the body fluid content and the like and adapt or amend automatically the treatment or certain parameters thereof or suggest to do so to the patient or the doctor if necessary to prevent harm or to improve the treatment outcome or both by controlling the dialysis apparatus effectively.

Many characteristics of the patient such as for example age, sex, weight, height and some other conditions such as changing sodium and water intake, position of the body, position of the electrodes during measurement and the like can have some effect on the measurement results. Hence, the accuracy of the bio-impedance measurement can be further improved if the bioelectrical impedance analyzer or body composition monitor comprises an input element for manually inputting at least some (or all) of the above mentioned conditions to the bio-impedance device or the body composition monitor, be it by the patient himself or by the medical staff.

If certain signals as related to herein are transmitted in a wireless manner, all advantages known to the skilled person can be achieved.

If the bio-impedance measuring device starts automatically measuring once the patient has placed, for example, his fingers on the electrodes, operating a switch for starting the measurement is no longer required. This can render the operation of the devices involved in the measurements less cumbersome. The patient may receive a signal, an alarm or the like once the measurement is finished, or not.

The electrodes according to the present invention can be advantageously used to upgrade conventional devices of the above mentioned group of electronic and/or non-electronic devices used in the preparation of a dialysis treatment or during dialysis, in particular by means of sticking or gluing them to said devices. For example, this can happen by using a pad comprising the electrodes. This way it is easy and also economical to achieve the advantages discussed above while maintaining existing devices that are already in operation.

If for starting the bioelectrical impedance and/or body composition measurement a disc with a dial or another element has to be inserted into or connected with the device according to the present invention, the patient would notice that he has forgotten to insert or connect the disc or the element since he would not be able to carry out measurements. This way, the risk of overlooking to insert of connect elements that have to be inserted or connected for a proper function of, e. g., the blood treatment apparatus or the extracorporeal blood circuit is reduced.

In the following, the present invention will be exemplarily specified with reference to the appended drawing. In the drawing, identical reference numerals designate same or identical elements.

DETAILED DESCRIPTION

Figure 1:
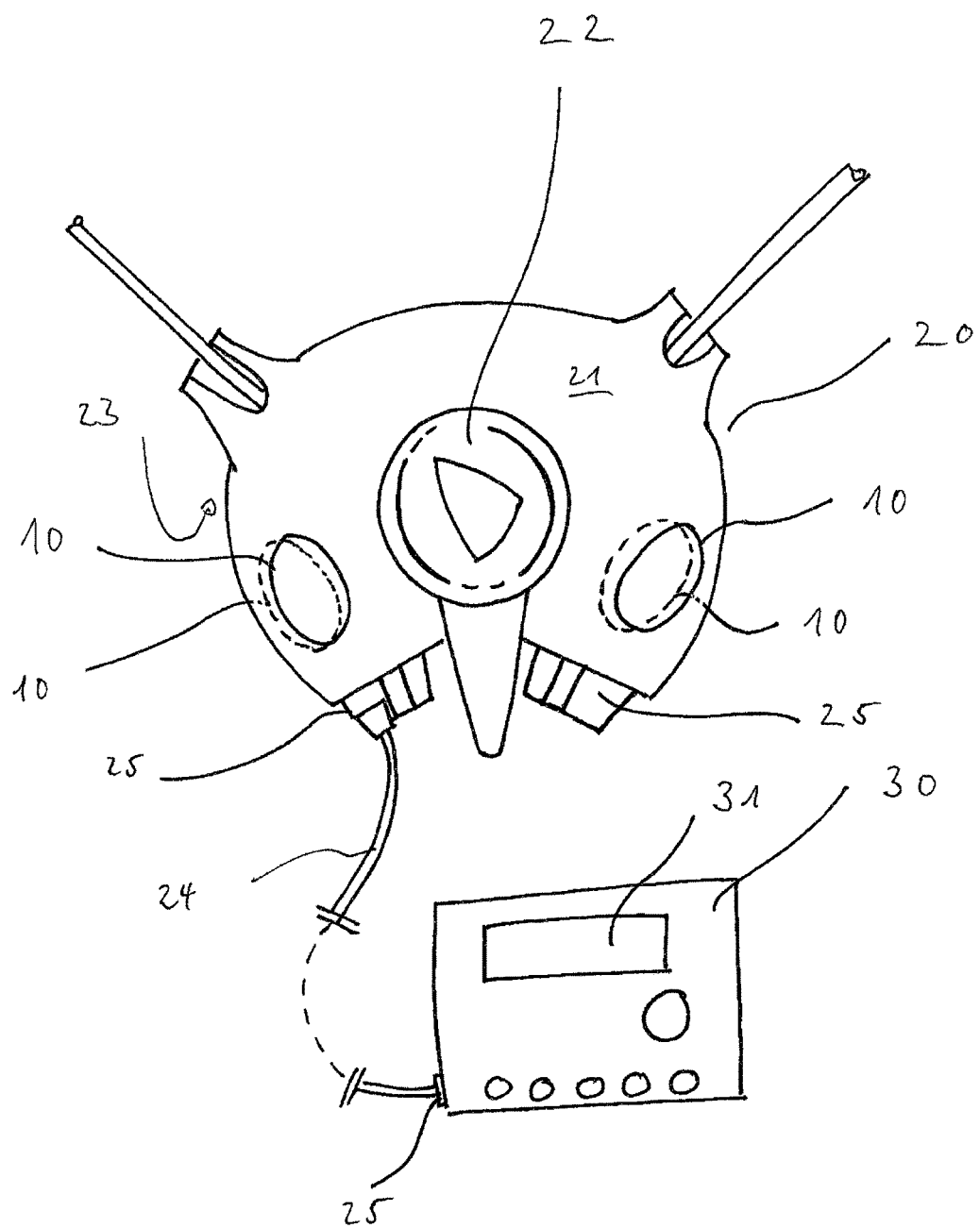
FIG. 1 shows a top view of an organizer according to the present invention having two electrodes on its upper side.

FIG. 1 schematically shows a top view of an organizer 20 in accordance with a first embodiment of the present invention having four electrodes 10. Below the organizer 20, FIG. 1 schematically shows a conventional bio-impedance measuring device 30.

Two of said electrodes 10 are placed on the top side 21 of the organizer 20, lateral to the disk having a dial 22 (the dial 22 also being called a stay safe connector herein). Two other electrodes 10 are placed on the bottom side 23 of the organizer 20 and shown by dotted lines in FIG. 1. This way, the organizer 20 comprises a first pair of electrodes 10 (left from the dial 22) and a second pair of electrodes 10 (right from the dial 22).

In order to check his body composition or bioelectrical impedance, the patient has to place his thumbs on the two electrodes 10 of the top side 21 and his forefingers on the two electrodes 10 of the bottom side 23 of the organizer 20 for a bio-impedance measurement. The electrodes 10 are placed in such a manner that the patient can hold the organizer 20 with two hands and can reach every electrode 10 with the corresponding finger without effort. The position of the particular finger on the electrode is pre-determined by the form, configuration, position and/or shape of the electrode 10. This pre-determination makes the measurement reliable and reproducible.

In the embodiment according to the present invention shown in FIG. 1, the organizer 20 is connected to the bio-impedance measuring device 30 and/or a body composition monitor by means of a connecting element 24 connected to or plugged into a terminal or notch 25 of the organizer 20. In alternative embodiments according to the present invention, a wireless connection is provided instead of the connecting element 24 shown in FIG. 1. By means of wireless connection, the patient is less hampered by electric wires.

In some embodiments according to the present invention like the one shown in FIG. 1, the bio-impedance measuring device 30 is turned on or starts measuring automatically by touching the four electrodes 10 with the fingers.

The result of the measurement can be displayed on the display 31 of the bio-impedance measuring device 30. The bio-impedance measuring device 30 can include an alarm modus to alert the patient if the results of measurements are below or above pre-determined target values or if the results do not make sense. The alarm signal or alert can reach only the patient, with a sound or a message on the display of the bio-impedance measuring device 30, or it can reach a medical monitoring centre. The same applies to the measurement results. They can also be transferred to the medical monitoring centre. In addition or as an alternative, the measurement results can be sent to the dialysis device. In particular embodiments, the measurement results sent to the dialysis device can be used to automatically control the treatment.

The bio-impedance measuring device 30 below the organizer 20 can be replaced for a body composition monitor.

Figure 2:
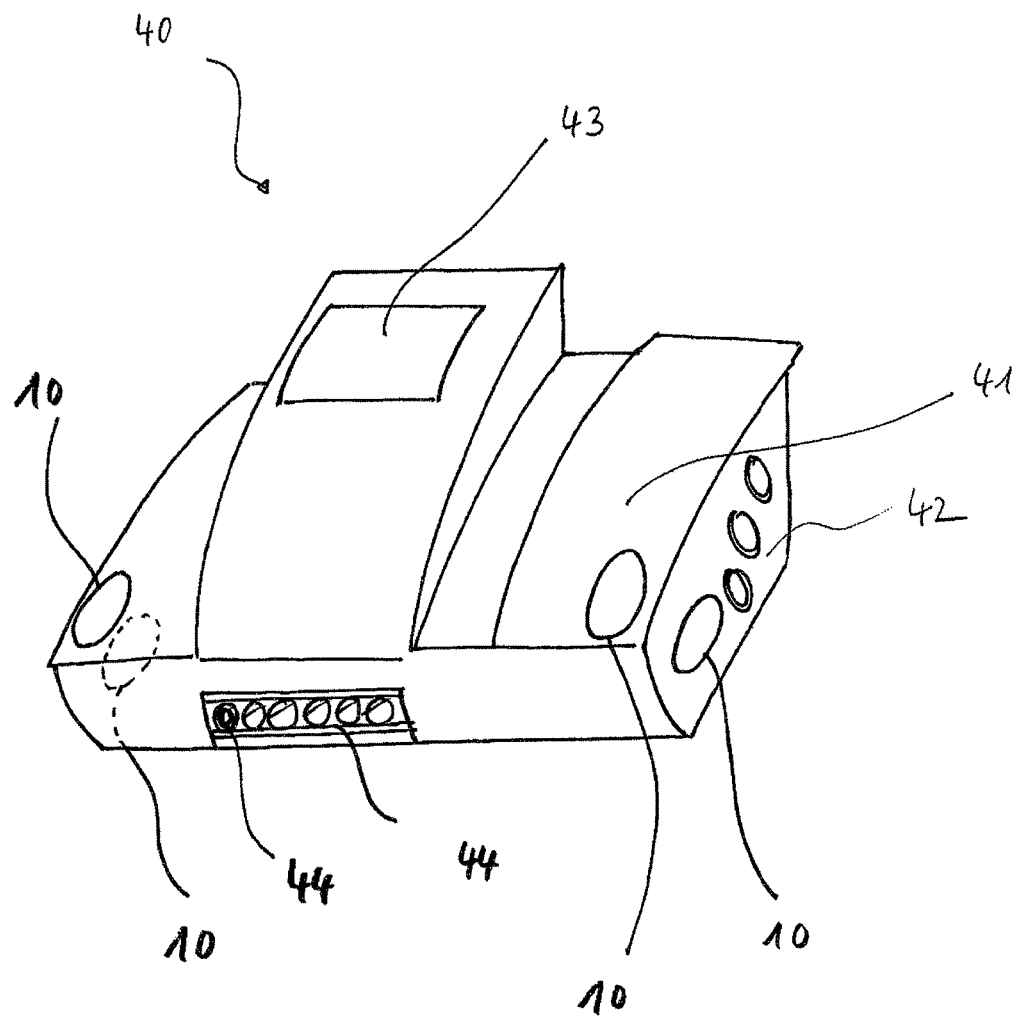
FIG. 2 shows a perspective view of an ADP-cycler according to the present invention having four electrodes.

FIG. 2 shows a perspective view of a conventional ADP-cycler 40 (automated peritoneal dialysis-cycler) according to the present invention having four electrodes 10 according to the present invention on its surfaces, the electrodes 10 being integral or attached to the ADP-cycler 40.

Two of the electrodes 10 are placed on the upper surface or upper part 41 of the ADP-cycler and another two on both lateral surfaces or lateral parts 42 (one of them being indicated by dotted lines), so that a patient can effortlessly reach the electrodes 10 of the upper part 41 of the device with his thumbs and the electrodes 10 of the lateral parts 42 with his forefingers or with his middle fingers.

Upon touching of the electrodes 10 or upon activating a switch or the like the measurement automatically takes place. The results of the measurement can be displayed on a display 43.

In this embodiment of the present invention the bio-impedance measuring device 30 is integrated into the ADP-cycler 40.

In other embodiments according to the present invention, the bio-impedance measuring device 30 is different from or non-integral with the ADP-cycler 40. It may be connected to the APD-cycler 40 by a connecting element 44.

A conventional ADP-cycler 40 can be upgraded or interlinked by means of wires or wireless with a separate bio-impedance measuring device 30 by attaching four electrodes 10 according to the present invention to the casing, housing or the like of the ADP-cycler 40.

Figure 3:
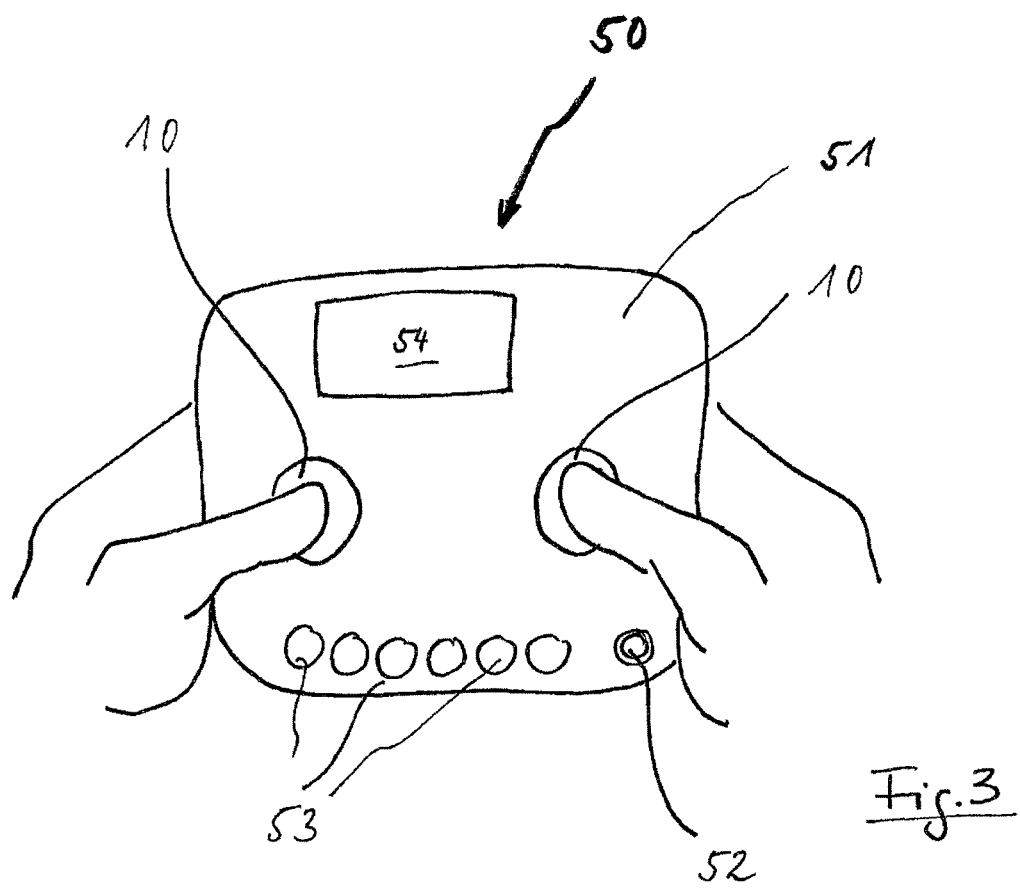
FIG. 3 shows a top view of a hand-held electrodes holder according to the present invention.

FIG. 3 shows a top view of a hand-held electrodes holder 50 according to the present invention. The representation of FIG. 3 shows two electrodes 10 for the thumbs of the patient. The embodiment of the hand-held electrodes holder 50 shown in FIG. 3 is quite simple. Simply spoken, it may be a casing 51 comprising the electrodes 10 on its surfaces.

The hand-held electrodes holder 50 may have terminals or sockets 52 for connecting the hand-held electrodes holder 50 to another apparatus, e.g., for connecting the electrodes 10 to a bio-impedance measuring device 30 by means of connecting elements not shown. In further embodiments according to the present invention, the connection is wireless. More sophisticated embodiments according to the present invention include an input element 53 for inputting patient-related information that can be helpful to achieve a more accurate measurement result such as, for example, height, sex, age, etc.

The hand-held electrodes holder 50 includes in certain embodiments according to the present invention a bio-impedance measuring device 30, too. In this case the patient may not need any device except for the hand-held electrodes holder 50 to perform a complete bio-impedance analysis.

The hand-held electrodes holder 50 according to the present invention may comprise a display 54.

Figure 4:
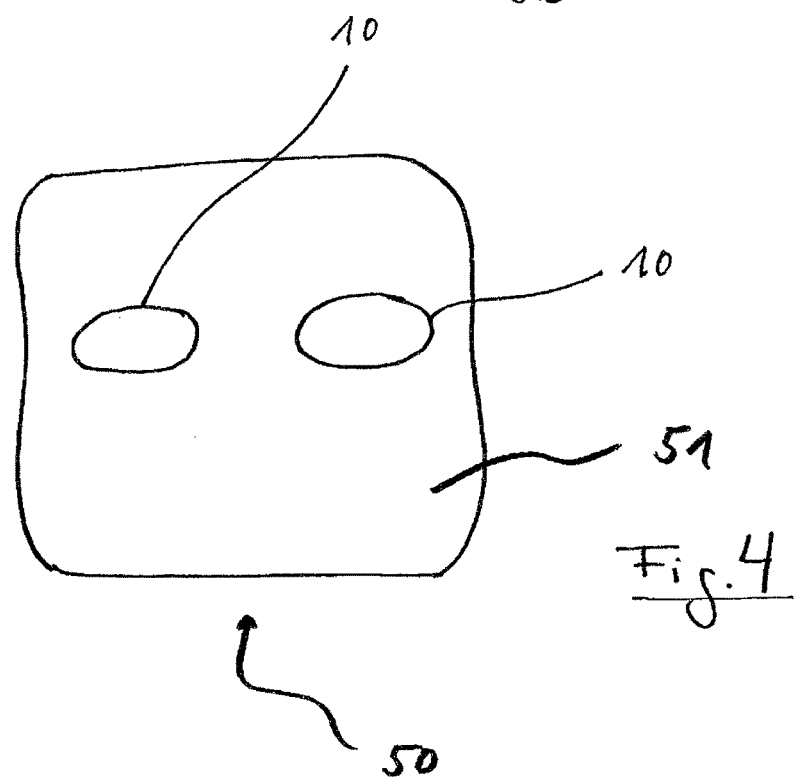
FIG. 4 shows a bottom view of the hand-held electrodes holder of FIG. 3.

FIG. 4 shows a bottom view of the hand-held electrodes holder 50 of FIG. 3. In FIG. 4, the two electrodes 10 for the forefingers or the middle fingers of the patient are shown.

Figure 5:
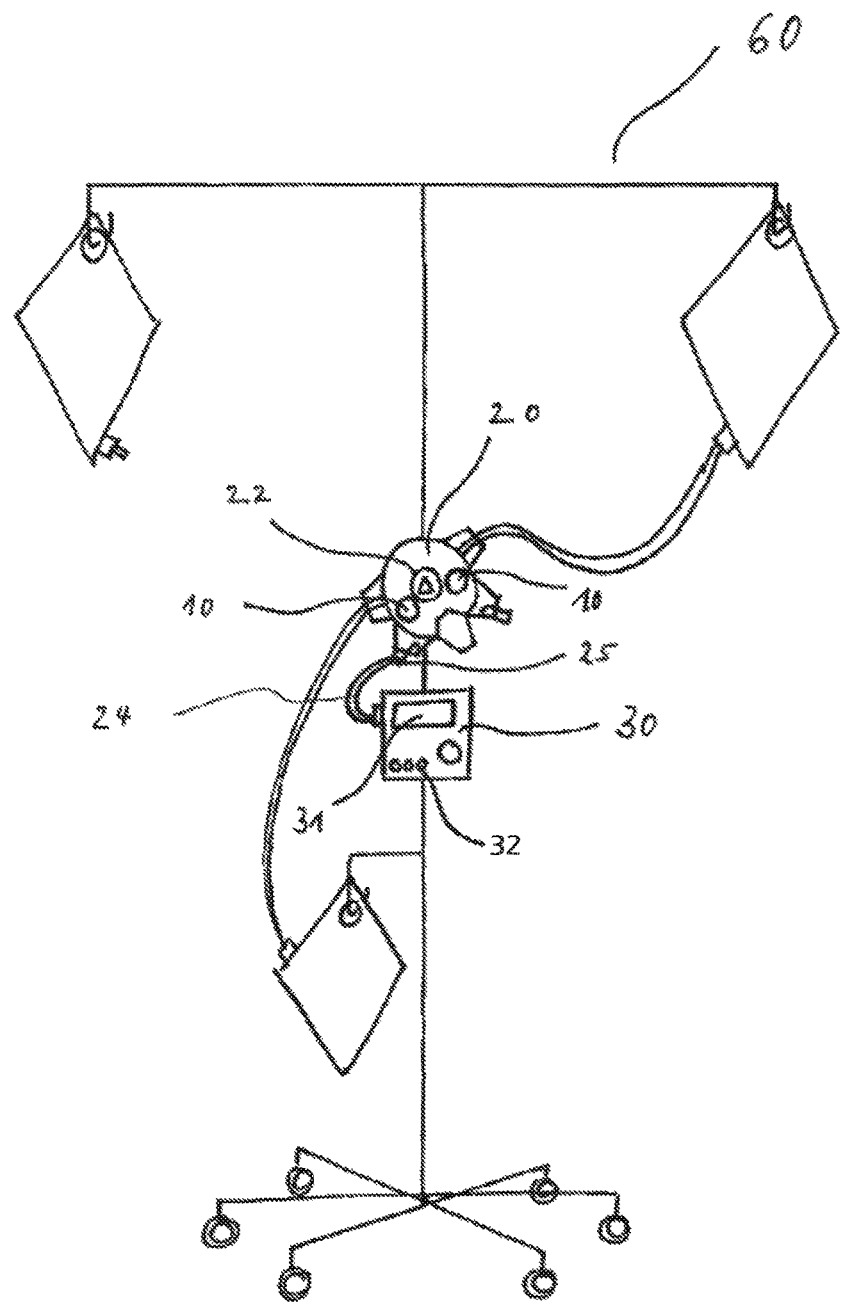
FIG. 5 shows schematically a perspective view of an organizer according to the present invention on a stand.

FIG. 5 shows an example of an organizer 20, which is held on a movable stand 60. The organizer 20 has four electrodes 10 positioned like in FIG. 2. The electrodes 10 are placed on the surface of the organizer 20 and are connected to a bio-impedance measuring device 30, which constitutes a separate unit from the organizer 20 and has been placed below it. The connection can be wireless.

The bio-impedance measuring device 30 can be embodied as in every other embodiment or configuration as shown by the figures or as described above.

REFERENCE NUMERALS LIST 10 electrodes
20 organizer
21 top side of the organizer
22 disk with dial
23 bottom side of the organizer
24 connecting element
25 terminal or notch
30 bio-impedance measuring device
31 display of the bio-impedance measuring device
32 alarm modus button
40 ADP-cycler 41 upper part of the ADP-cycler
42 lateral parts of the ADP-cycler
43 display of the ADP-cycler
44 connecting element of the ADP-cycler
50 hand-held electrodes holder
51 casing
52 connecting element of the hand-held electrodes holder
53 input element
54 display of the hand-held electrodes holder
60 stand

The invention claimed is:

1. A device configured to determine a bio-impedance or a body composition of a patient in preparation of, or during, a peritoneal dialysis treatment, comprising:
four electrodes, each electrode being integral with a surface of (i) an organizer of a continuous ambulatory peritoneal dialysis system (CAPD), (ii) an automated peritoneal dialysis device, or (iii) an automated peritoneal dialysis-cycler (APD-Cycler),
wherein the device is configured to start measuring or to allow measuring the bio-impedance or the body composition, or both, upon or by inserting a disc with a dial into the device, wherein the dial is rotatable relative to the disc for selecting between two or more operating states of the device.

2. The device of claim 1, wherein each electrode is a reusable electrode.

3. The device of claim 1, wherein the four electrodes includes a first electrode and a second electrode, the first and second electrodes spaced apart from each other at a distance of 2.5 to 15 cm.

4. The device of claim 3, wherein the first and second electrodes are spaced apart from each other at a distance of 4 to 7.5 cm.

5. The device of claim 3, wherein the first and second electrodes are arranged on different housing surfaces of the CAPD, the peritoneal dialysis device, or the APD-Cycler.

6. The device of claim 1, wherein the CAPD, the peritoneal dialysis device, or the APD-Cycler has at least one connection element configured to connect the CAPD, the peritoneal dialysis device, or the APD-Cycler to at least one of a (a) bio-impedance device or (b) body composition monitor.

7. A system for determination of a bio-impedance or a body composition of a patient in preparation of, or during, a peritoneal dialysis treatment, comprising:
a device comprising:
four electrodes, each electrode being integral with a surface of (i) an organizer of a continuous ambulatory peritoneal dialysis system (CAPD), (ii) an automated peritoneal dialysis device, or (iii) an automated peritoneal dialysis-cycler (APD-Cycler); and
at least one of a (a) bio-impedance device and a (b) body composition monitor,
wherein the at least one of the (a) bio-impedance device and the (b) body composition monitor is connected to the CAPD, the peritoneal dialysis device, or the APD-Cycler of the device, and
wherein the device is configured to start measuring or to allow measuring the bio-impedance or the body composition, or both, upon or by inserting a disc with a dial into the device, wherein the dial is rotatable relative to the disc for selecting between two or more operating states of the device.

8. The system of claim 7, wherein the system is configured to measure the bioelectrical impedance or the body composition, or both, upon touching of the four electrodes while the disc with the dial is inserted the device.

9. The system of claim 7, further comprising:
a device configured to send measurement data to at least one of (i) a dialysis apparatus, (ii) a medical monitoring center, or (iii) a medical card of the patient.

10. A dialysis apparatus in signal communication with the system of claim 7 and configured to receive measurement results from the four electrodes.

11. The dialysis apparatus of claim 10, comprising:
a control unit, the control unit configured to control the peritoneal dialysis treatment based on the measurement results from the four electrodes.

12. A method for determining parameters for estimating a hydration or a nutritional status of a dialysis patient, the method comprising the steps of:
touching, by at least two body portions of the patient, at least two electrodes of a device comprising four electrodes, each electrode being integral with a housing surface of (i) an organizer of a continuous ambulatory peritoneal dialysis system (CAPD), (ii) an automated peritoneal dialysis device, or (iii) an automated peritoneal dialysis-cycler (APD-Cycler), each of the electrodes being in communication with at least one of a (a) bio-impedance device and a (b) body composition monitor, wherein the bio-impedance device and the body composition monitor are configured to start measuring or to allow measuring the bio-impedance or the body composition, respectively, upon or by inserting a disc with a dial therein, wherein the dial is rotatable relative to the disc for selecting between two or more operating states of the device;
processing data received from the electrodes in a processing element of the at least one of the (a) bio-impedance device and the (b) body composition monitor; and
sending the processed data from the (a) bio-impedance device or the (b) body composition monitor to at least one of (i) a dialysis apparatus, (ii) a medical monitoring centre, and (iii) a medical card of the patient.

13. The method of claim 12, further comprising:
adjusting at least one treatment parameter of a dialysis treatment based upon the processing of the data by the processing element.

14. The method of claim 13, further comprising:
automatically adjusting or controlling the dialysis treatment based upon the processing of the data by the processing element.

15. A non-transitory computer-readable storage medium with an executable program stored thereon, wherein the program instructs a programmable computer system so as to execute the steps of the method according to claim 14.

* * * * *